United States Patent
Gdaniec

(10) Patent No.: US 11,515,015 B2
(45) Date of Patent: Nov. 29, 2022

(54) MEDICAL DEVICE AND MOBILE DEVICE FOR ASSIGNING PHYSIOLOGICAL PATIENT DATA TO A PATIENT IDENTIFICATION

(71) Applicant: Drägerwerk AG & Co. KGaA, Lübeck (DE)

(72) Inventor: Przemyslaw Gdaniec, Stockelsdorf (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 1088 days.

(21) Appl. No.: 15/690,553

(22) Filed: Aug. 30, 2017

(65) Prior Publication Data

US 2018/0060498 A1 Mar. 1, 2018

(30) Foreign Application Priority Data

Aug. 31, 2016 (DE) ...................... 10 2016 010 480.5

(51) Int. Cl.
*G16H 40/63* (2018.01)
*G16H 10/60* (2018.01)
(Continued)

(52) U.S. Cl.
CPC ......... *G16H 10/60* (2018.01); *G06K 19/0704* (2013.01); *G06K 19/0723* (2013.01); *G16H 30/20* (2018.01); *G16H 40/63* (2018.01)

(58) Field of Classification Search
CPC ........ G16H 10/60; G16H 40/60; G16H 40/63; G16H 40/67; G06F 19/321; G06K 19/0723

See application file for complete search history.

(56) References Cited

U.S. PATENT DOCUMENTS

2004/0100361 A1* 5/2004 Brackett ................ G06K 17/00 340/5.74
2006/0246921 A1* 11/2006 Russ ...................... A61B 5/002 455/456.5

(Continued)

FOREIGN PATENT DOCUMENTS

DE 101 54 908 A1 4/2003
DE 103 54 929 A1 7/2004
DE 11 2006 000 953 T5 3/2008

*Primary Examiner* — Jonathan Durant
(74) *Attorney, Agent, or Firm* — McGlew and Tuttle, P.C.

(57) ABSTRACT

A medical device has a sensor interface, a data network interface, a wireless interface, a computer, and a touch-sensitive display unit. The sensor interface detects a sensor signal indicative of at least one physiological parameter of a patient. The computer provides medical data derived from the sensor signal via the data network interface. The wireless interface receives wireless signals indicative of patient identification of a mobile device carried on the patient. The computer selects a patient identifications subset based on the wireless signals as well as determining respective image data sets based on the selected patient identifications and actuates the display unit to display respective image data sets in respective display fields and to derive a selection of a certain image data set based on a signal provided by the display unit, and to provide the identification assigned to the image data set via the data network interface.

16 Claims, 4 Drawing Sheets

(51) Int. Cl.
 *G06K 19/07* (2006.01)
 *G16H 30/20* (2018.01)

(56) References Cited

U.S. PATENT DOCUMENTS

| | | | |
|---|---|---|---|
| 2012/0003933 A1* | 1/2012 | Baker | A61B 5/021 |
| | | | 455/41.2 |
| 2013/0109929 A1* | 5/2013 | Menzel | A61B 90/98 |
| | | | 600/301 |
| 2014/0278524 A1* | 9/2014 | Vaglio | A61B 5/681 |
| | | | 705/3 |
| 2015/0065989 A1* | 3/2015 | Moberg | G08C 17/02 |
| | | | 604/500 |
| 2015/0302539 A1* | 10/2015 | Mazar | G16H 40/20 |
| | | | 705/3 |

* cited by examiner

MEDICAL DEVICE AND MOBILE DEVICE FOR ASSIGNING PHYSIOLOGICAL PATIENT DATA TO A PATIENT IDENTIFICATION

CROSS REFERENCE TO RELATED APPLICATIONS

This application claims the benefit of priority under 35 U.S.C. § 119 of German Application 10 2016 010 480.5 filed Aug. 31, 2016, the entire contents of which are incorporated herein by reference.

FIELD OF THE INVENTION

The invention relates to medical devices in general and more particularly to a medical device having one or more sensor interface, a data network interface, a wireless interface, a computer and a touch-sensitive display unit.

BACKGROUND OF THE INVENTION

It is common in the field of medicine, such as hospitals, to detect physiological parameters or physiological signals of a patient. It is necessary in this connection to unambiguously assign the detected physiological parameters or the detected physiological data to a patient. A medical device may then provide the detected physiological signals or physiological data via, for example, a data network interface.

If a medical device for detecting the physiological data or physiological parameters of a patient shall be used, these data or signals are usually displayed on a display unit of the medical device. It is advantageous in this connection, for example, to display the name of the patient or his identification together with the data or the signals.

Provisions are made in this connection in conventional solutions for a patient to be picked out of a data bank and then selected by a user by means of a display unit and an input unit at the medical device. To display the name and the identification of the patient on the display unit, such identification must possibly be displayed in its full length and it must therefore possibly be keyed in or entered during the search operation, which is sometimes cumbersome. If the name or the identification of the patient is then displayed, the patient can then be selected by the user from a total set of potential patient identifications or potential patient names, for example, by pressing an enter key or a confirmation key. It is possible in this connection that the medical device polls stored patient identifications or patient data from a memory unit of its own, or from a memory unit, e.g., data bank, which can be reached via a data network interface. It is consequently necessary at times to take into account a relatively large amount of potential patient names or potential patient identifications during the assignment operation and the entry on the medical device by the user.

Such an assignment of a patient to a medical device may therefore require a cumbersome entry procedure by the user.

SUMMARY OF THE INVENTION

An object of the present invention is to provide a mobile device, which can be carried on the body of a patient, and the assignment of a patient identification to the medical device can be performed in an automated and simplified manner.

This object according to the present invention is accomplished by a medical device having at least one sensor interface, a data network interface, a wireless interface, a computer and a touch-sensitive display unit. The sensor interface is configured to detect a sensor signal, which indicates at least one physiological parameter of a patient. The computer is configured to provide medical data derived from the sensor signal via the data network interface. The wireless interface is configured to receive a plurality of wireless signals, which indicate each a respective patient identification of a respective mobile device that can be carried on the body of the patient. The computer is configured to select a preferred subset of the patient identifications on the basis of the wireless signals, to directly or indirectly to determine respective data sets on the basis of the selected patient identifications, further to actuate the display unit such that the respective image data sets are displayed in respective display fields, further to derive a selection of a certain image data set on the basis of a signal provided by the display unit, and finally to provide the patient identification assigned to the selected image data set via the data network interface.

The medical device according to the invention is advantageous because assignment of the medical device to a patient identification or to a patient is made possible hereby in an automated manner, and only patient identifications that are selected into the preferred subset on the basis of the wireless signals of the mobile devices are taken into account. Consequently, it is not necessary to take into account for the assignment of the medical device to the patient identification all the potential patients who are located in an entire data bank of a clinical setting or hospital. Only patient identifications of the wireless signals do actually lead to the selection of the corresponding patient identification into the subset of the patient identifications are taken into account.

Further, the medical device according to the invention is especially advantageous because it is possible for a clinician to assign the patient to be selected, or the patient's identification, to the medical device by selecting the corresponding image data set by means of touching the corresponding display field. This assignment of the patient identification to the medical device can then be provided, for example, for a server via the data network interface.

Further, a mobile device is provided, which can be carried on the body of a patient or physically associated with the patient. The mobile device has a wireless interface, a computer, a memory unit and at least one display unit. The computer is configured to send via the wireless interface a wireless signal, which indicates a patient identification being stored in the memory unit, further to directly or indirectly determine an image data set on the basis of the patient identification as well as to actuate the display unit such that the image data set is displayed, and further to receive a confirmation signal via the wireless interface and to bring about the output of an optical confirmation signal via the at least one display unit upon receiving the confirmation signal.

Consequently, if the determination of the image data set is performed in the medical device in the same manner as in the mobile device, the same image data set is displayed in the display unit of the mobile device as in the display unit of the medical device. As a result, a clinician can then assign a patient, whose identity is known to the clinician, to the medical device in a simple and automated manner because the clinician only has to compare the image or the image data set that is displayed on the display unit of the mobile device with the image data set that is displayed in a display field of the display unit of the medical device.

If the clinician is certain of the identity of the patient, it is sufficient for the clinician, for control, simply to compare the image data sets in the display units of the mobile device and of the medical device in order to assign the patient or his patient identification to the medical device.

The computer is further preferably configured to determine a preferred sequence of the image data sets on the basis of the wireless signals as well as to actuate the display unit such that the respective image data sets are displayed as a function of the determined sequence.

This configuration of the medical device is advantageous because, for example, the image data set that corresponds to the identification with the strongest wireless signal can be displayed as the first image data set in case of wireless signals of different intensities. For example, a patient identification for which the corresponding patient is located in the immediate vicinity of the medical device can thus be displayed first by means of an image data set.

The medical device preferably has a memory unit, and the computer is further configured to store the assigned patient identification in the memory unit.

This configuration of the medical device is advantageous because the assigned patient identification can still be used later, e.g., for the purpose of a display together with physiological data on the display unit of the medical device. It is further possible that the stored, assigned patient identification can be polled via the data network interface by a server from the medical device in order to also obtain the patient identification assigned to the medical device at a later date.

The computer is further preferably configured to determine the respective image data sets directly from the respective patient identifications on the basis of predefined determination steps.

This configuration of the present invention makes it possible to derive an image data set directly from a patient identification, for example, on the basis of a hash value determination, without having to make use of another device for this, for example, a server system. As a result, it is made hereby possible for the medical device to be independent for the step of determining the image data set or image data sets of other network units.

The computer is further preferably configured to determine the respective image data sets indirectly from the respective selected patient identifications by the computer transmitting the respective selected patient identifications via the data network interface to a server and by receiving the respective image data sets from the server via the data network interface.

It is possible according to this configuration that the computer does not have to determine the image data sets itself but receives these from the server. As a result, the computer must provide a reduced computing capacity only and can transfer the step of determination of the image data sets from the patient identifications to another unit, for example, a server.

The computer is further preferably configured for sending a confirmation signal via the wireless interface to the device whose image data set is considered to be selected.

This configuration of the present invention is advantageous because the medical device thus informs the mobile device about the fact that it was selected for the patient identification.

The computer is preferably configured to receive a reconfirmation signal from the device via the wireless interface and to perform the providing of the assigned patient identification only after receiving the reconfirmation signal.

This configuration of the present invention is advantageous because the patient identification is actually provided to a server in the network only after the medical device has been finally assigned to the mobile device. A situation in which the mobile device has not yet finally confirmed the assignment is avoided hereby.

The mobile device is preferably configured such that the at least one display unit is given by a display and an LED, and the computer of the mobile device is further configured to actuate the display such that the image data set is displayed, and to bring about the output of the optical confirmation signal via the light-emitting diode.

This configuration of the mobile device is advantageous because the display can be used to display the image, while a separate unit in the form of the LED can elicit an increased attention of the user in order to indicate or display the confirmation by the medical device.

The mobile device is preferably configured such that the computer is further configured to send a reconfirmation signal via the wireless interface after receiving the confirmation signal.

This configuration of the mobile device is advantageous because the medical device is informed hereby about the fact that the mobile device has accepted the assignment.

The mobile device is preferably configured such that the computer is further configured to determine the image data set directly from the patient identification on the basis of predefined determination steps.

This configuration is advantageous because it makes it possible, for example, on the basis of a hash value determination, to derive an image data set from a patient identification without having to use another device, for example, a server system, in the process. The independence of the medical device for the step of determining the image data set or the image data sets from another network unit is made possible hereby.

The mobile device is preferably configured such that the computer is further configured to determine the image data set indirectly from the patient identification by the computer reading the image data set from the memory unit as a data set assigned in the memory unit to the patient identification.

This configuration of the mobile device is advantageous because it is possible hereby for the computer not to have to determine the image data sets itself, but to receive these from the server. As a result, the computer must provide a reduced computing capacity only and can transfer the step of determining the image data sets from the patient identifications to another network unit, for example, a server.

The present invention will be explained in more detail below on the basis of special embodiments without limitation of the general inventive idea. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
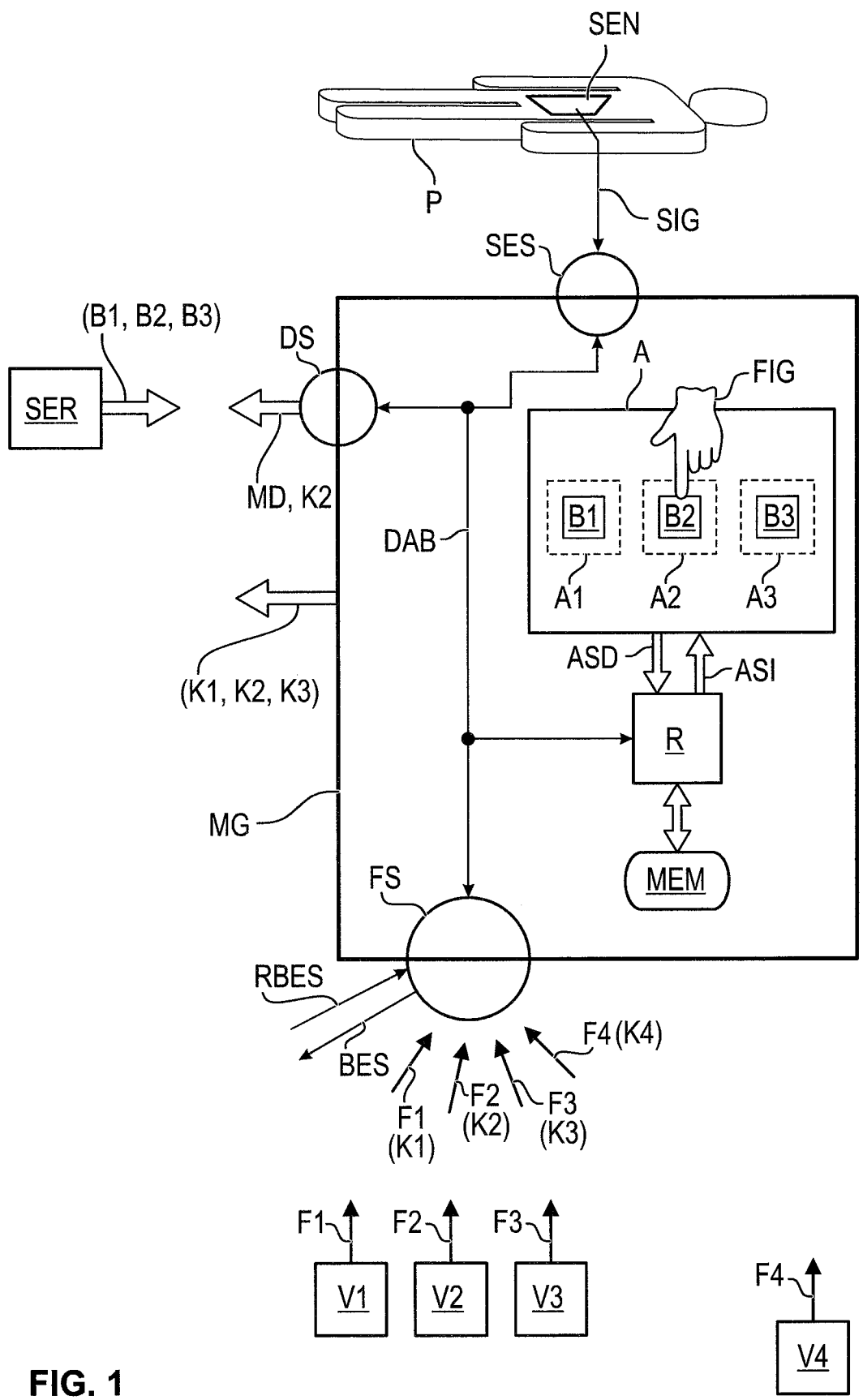
FIG. 1 is a schematic view showing an embodiment of the medical device according to the present invention.

Referring to the drawings, FIG. 1 shows an embodiment of the medical device MG according to the invention.

A medical device in the sense of the present invention is a device which detects physiological signals or sensor signals, which indicate at least one physiological parameter of a patient. A medical device may be, for example, a ventilator (also known as a medical respirator), an anesthesia apparatus, an incubator or a so-called patient monitor for detecting physiological signals.

The medical device MG has at least one sensor interface SES, via which a sensor signal SIG from a sensor SEN can be detected. The sensor signal SIG indicates at least one physiological parameter of a patient P.

A computer R is configured to derive medical data from the sensor signal SIG and to provide them to a data network via a data network interface DS.

The medical device MG further has a wireless interface FS.

The medical device MG further has a touch-sensitive display unit A.

At least the sensor interface SES, the data network interface DS, the wireless interface FS as well as the computer R are connected to one another via an internal data bus DAB.

The display unit A may be actuated by means of a display signal ASI by the computer R.

The medical device MG preferably has a memory unit MEM.

In addition to the medical device MG, a server SER is shown, with which the medical device MG can communicate by means of the data network interface DS.

FIG. 1 further shows mobile devices V1, . . . , V4. These mobile devices are mobile in the sense that they can be carried on the body of a patient.

The mobile devices V1, . . . , V4 send respective wireless signals F1, . . . , F4, which are received by the wireless interface FS.

The wireless signals F1, . . . , F4 indicate respective patient identifications K1, . . . , K4.

A patient identification K1, . . . , K4 may be an unambiguous identification of a patient in the form of a data set. This data set may consist either of patient data themselves or of data that are derived from patient data. The patient identification is preferably a hash value, which was derived from a patient data set.

The sensor interface SES receives from the physiological sensor SEN the sensor signal SIS, which indicates a physiological parameter of the patient P, for example, the blood pressure, blood oxygen level, heart rate or similar physiological parameters.

The medical data MD, which are derived by the computer R from the sensor signal SIS, are corresponding physiological data, which correspond to the physiological sensor signal SIS.

The data network interface DS may be a wired or else a wireless data interface. The data network interface is preferably an IP interface, an Ethernet interface or a WLAN interface.

The touch-sensitive display unit A may be a pressure-sensitive or capacitively sensitive display unit, which can detect touches, for example, by a human finger FIG. in a corresponding display field A1, A2, A3. The display unit A is preferably a so-called touchscreen.

The mobile devices V1, . . . , V4 are preferably wristbands, which are carried by respective patients on their wrists. The mobile devices are physically associated with the patient body and preferably and advantageously that are carriable on a patient body.

The mode of operation of the medical device MG according to the present invention for assigning a patient identification K1, . . . , K4 to the medical device MG will now be explained in more detail.

The wireless interface FS receives the wireless signals F1, . . . , F4 of the devices V1, . . . , V4.

Based on these wireless signals F1, . . . , F4, the computer R first determines the patient identifications K1, . . . , K4, which are indicated by the wireless signals.

If, for example, a patient, who carries the device V4, is located at a markedly greater distance from the medical device MG than are the patients carrying the other devices V1, V2, V3, it could be advantageous to make possible only the assignment of the identifications K1, K2, K3 of the corresponding patients to the medical device MG, so that it would not thus be possible to assign too many patient identifications to the medical device MG by the automated method according to the invention. This leads to the simplicity of the assignment of a patient identification to the medical device MG because not all the patients theoretically located in the clinical setting or hospital with their corresponding identifications are accessible to this assignment process according to the present invention.

Based on the wireless signals F1, . . . , F4, the computer R consequently selects a preferred subset K1, K2, K3 of the patient identifications K1, . . . , K4. This selection of the preferred subset K1, K2, K3 may take place, for example, in such a manner that the computer R determines the respective signal intensities of the respective wireless signals F1, . . . , F4 and then takes into account only the identifications K1, K2, K3, for which the corresponding wireless signals F1, F2, F3 exceed a minimum wireless signal intensity.

As an alternative, the selection of the subset of patient identifications K1, K2, K3 may take place in such a way that a so-called run time measurement is performed by the computer R on the basis of the wireless signals F1, F2, F3, F4, so that the computer R can infer a distance of the corresponding computer V1, . . . , V4, which sent the corresponding wireless signals F1, . . . , F4. If the distance of the corresponding device, which was determined by the computer R, now exceeds a predefined maximum distance value, the corresponding identification K4 of the wireless signal F4 of the device V4 will not be taken into account.

The computer R determines respective image data sets B1, B2, B3 in a direct or indirect manner on the basis of the selected patient identifications K1, K2, K3. This step of the determination will be explained in detail later.

The respective image data sets B1, B2, B3 are then displayed in respective display fields A1, A2, A3 of the display unit A by the computer R correspondingly actuating the display unit A. This is preferably carried out by the actuating signal ASI, which is provided by the computer R for the display unit A.

The display unit A provides a signal ASD to the computer, which signal indicates the touching of a corresponding display field A2 by a finger FIG. or another extremity of a user. Based on the signal ASD provided by the display unit A, the computer R derives the selection of a certain image data set B2.

Since the computer R controls the display of image data sets B1, B2, B3 by means of its actuating signal ASI in the display fields A1, A2, A3 of the display unit A, the computer R can consequently derive the particular image data set B2 that was selected from the signal ASD, which indicates the touching of a display field A2. In other words, the computer R detects the touching of a display field A2 on the basis of the signal ASD and derives the selection of the image data set B2 from the touching of a display field A2 on the basis of the signal ASD.

Finally, the computer R provides via the data network interface DS the patient identification K2 that was assigned to the selected image data set B2 or corresponds to this.

Consequently, the user must only check whether the displayed image data set BX of the mobile device MV is displayed on the display unit A of the medical device MG and by selecting the corresponding display field A2 with the user's finger FIG. and by touching the display field A2 on the display unit A, the user can then assign the patient with the patient's identification, with corresponding image data set B2 being displayed in the display field A2, to the medical device MG. Consequently, if the image data set BX from FIG. 2 and the image data set B2 from FIG. 1 match, the user of the mobile device MV from FIG. 2 with his patient identification is assigned to the medical device MG.

Figure 2:
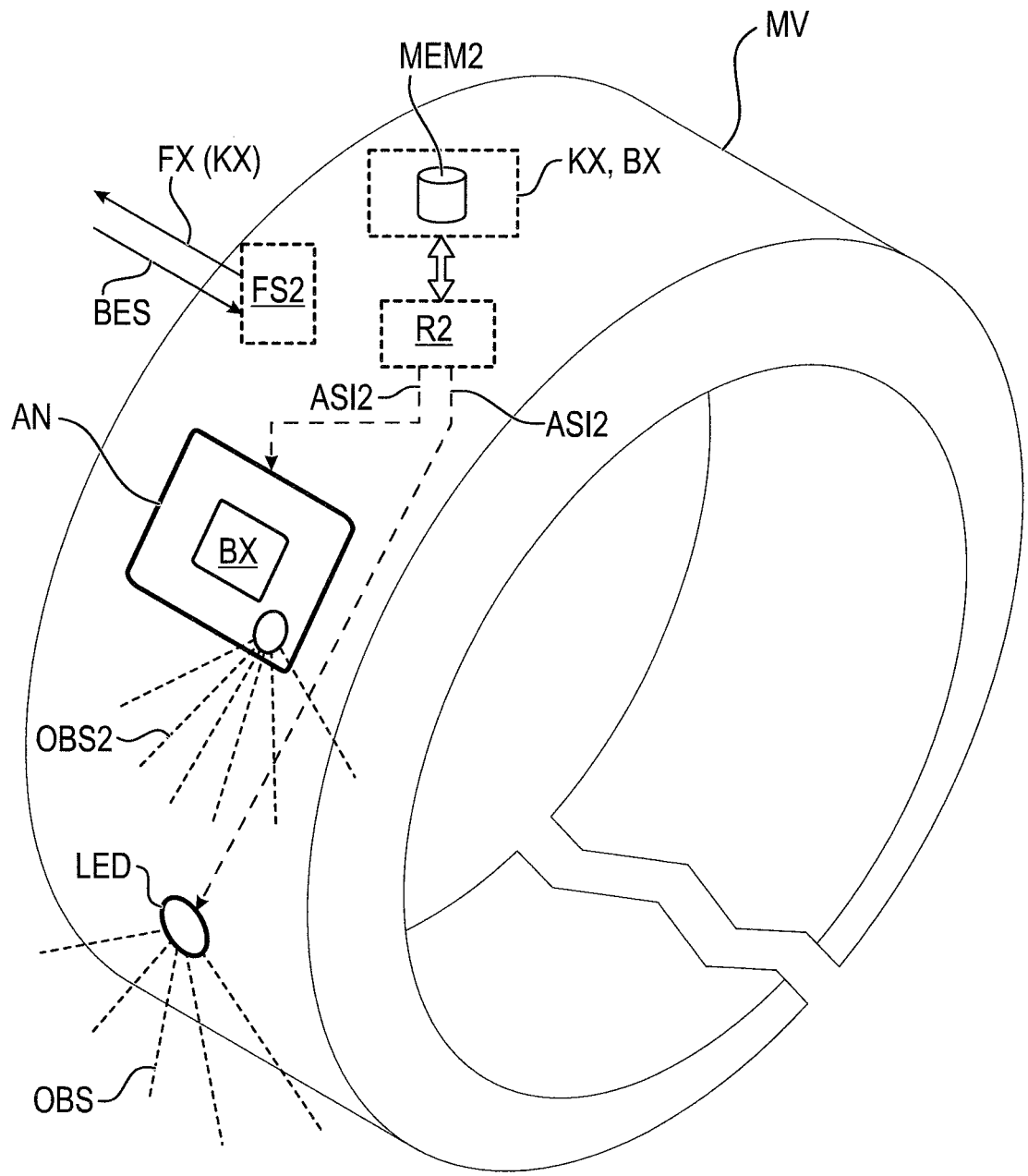
FIG. 2 is a schematic view showing an embodiment of the mobile device according to the present invention, which can be carried on the body of a patient.

FIG. 2 shows an advantageous embodiment of a mobile device according to the present invention, which may be one of the devices V1, V2, V3, V4 from FIG. 1.

The mobile device MV can be carried on the body of a patient. The mobile device MV is preferably a wristband, which can be carried on a wrist of a patient.

The mobile device MV has a wireless interface FS2.

The mobile device MV has a computer R2 as well as a memory unit MEM2, which is connected to the computer R2 for data technology.

The mobile device MV has at least one display unit AN, LED. The display nit AN, LED may be actuated by the computer R2 by means of a control signal ASI2.

The at least one display unit AN, LED has at least one display AN. The mobile device MV further has preferably a display unit in the form of a light-emitting diode LED.

The computer R2 is configured to send, via the wireless interface FS2, a wireless signal, which indicates a patient identification KX being stored in the memory unit MEM2.

This mobile device MV may consequently be assigned to a very specific patient in terms of the patient identification KX in a previously possible configuration step of the memory unit MEM2. Consequently, if different patient identifications are sent to different mobile devices with their corresponding memory units, for example, by a central data system of a hospital, the assignment of a patient or of the identification of the patient according to the present invention to a medical device can then be carried out successfully. It is only necessary for different mobile devices with their corresponding memory units to have different patient identifications.

The mobile device MV or the mobile device computer R2 directly or indirectly determines an image data set BX on the basis of the patient identification KX. The computer R2 is further configured to actuate the display unit AN such that the image data set BX is displayed. The determination of the image data set BX from the patient identification in a direct or indirect manner will still be discussed more specifically later.

The mobile device MV being shown here may consequently be integrated with the medical device MG explained in reference to FIG. 1 in order to make possible the unambiguous assignment of a patient identification to the medical device MG.

The computer R of the medical device MG from FIG. 1 is further configured to determine a preferred sequence of the image data sets B1, . . . , B3 on the basis of the wireless signals F1, . . . , F4 and to actuate the display unit A such that the data sets B1, . . . , B3 are displayed as a function of the determined sequence.

For example, the computer R can use the corresponding wireless signal intensities of the respective wireless signals F1, . . . , F3 to determine the preferred sequence of the image data sets B1, . . . , B3.

This is advantageous because the device that is located, e.g., closest to the wireless interface FS or to the medical device MG is displayed as the first device by means of its corresponding image data set, so that such a device is also optically detectable as the first one for the user on the display unit.

The assigned patient identification K2 may be stored in the memory unit MEM.

The image data sets B1, . . . , B3 can be determined directly from the respective patient identifications K1, . . . , K3 on the basis of predefined determination steps in such a manner that these determination steps are stored in the form of software on the computer R. The software may also be stored, for example, in the memory unit MEM and provided for the computer R. These predefined determination steps make it possible to derive an image data set B1, . . . , B3 from the corresponding identification K1, . . . , K3 by these corresponding algorithmic steps. These predefined determination steps are such that corresponding respective different image data B1, B2, B3 are derived for mutually different, respective identifications K1, K2, K3.

In case the patient identification is a hash value on the basis of patient data, corresponding, unambiguous image data can be derived by the predefined determination steps. Such an image data element is, for example, a so-called "Identicon." An image data element or an image data set is consequently an unambiguous, visual representation of the unambiguous identification of the patient.

This configuration is advantageous because the computer R itself can derive the corresponding image data set B1, B2, B3 itself from the patient identification K1, K2, K3 on the basis of the predefined determination steps without having to use a separate unit, for example, the server SER, here.

The computer R preferably determines the respective image data sets B1, B2, B3 indirectly from the respective selected patient identifications K1, K2, K3 by the computer R transmitting the respective identifications K1, K2, K3 via the data network interface DS to another unit, for example, the server SER. The computer R then receives the respective image data sets B1, B2, B3 from the server via the data network interface DS.

This is advantageous because the computer R does not have to perform the determination of the image data sets B1, B2, B3 itself, for example, by using predefined determination steps in this configuration, but the computer R only must send the corresponding identifications K1, K2, K3 in order to then receive the image data sets B1, B2, B3. Consequently, the server makes available the corresponding visual representations or image data sets B1, B2, B3. The computer R preferably sends a confirmation signal BES via the wireless interface FS to the device V2 whose image data set B2 is considered to be selected.

This is advantageous because the corresponding device V2, which is considered to be selected for the computer R, is informed hereby that it was selected.

This could therefore be advantageous because the mobile device V2 could now put itself into a mode or operating state in which it does not become subject to any further assignment to, for example, another medical device.

If the mobile device MV according to FIG. 2 receives the confirmation signal BES via its corresponding wireless interface FS2, it brings about the output of an optical confirmation signal OBS, OBS2 via the at least one display unit AN, LED upon receiving the confirmation signal BES.

The optical confirmation signal OBS may be outputted here via, for example, the LED as a display unit. As an alternative or in addition, an optical confirmation signal OBS2 may also be outputted on a display AN.

This is advantageous because the medical device MV thus shows to the user via the at least one display unit AN, LED that this mobile device MV was selected on a medical device MG and the corresponding patient identification KX was assigned to the medical device.

The computer R of the medical device MG from FIG. 1 is preferably configured to receive a reconfirmation signal RBES from the device V2 via the wireless interface FS and to perform the providing of the assigned patient identification KS only after receiving the reconfirmation signal RBES.

This is advantageous because the assigned patient identification is provided via the data network interface DS only when the corresponding device V2 has also confirmed this assignment.

As a result, a situation is avoided in which the computer R of the medical device MG could assume that a device V2 and the corresponding patient identification K2 thereof is finally assigned to the medical device MG, but the device has no knowledge of it. Since the providing of the patient identification K2 is performed only when the reconfirmation signal RBES of the device V2 is received, it is ensured that the device V2 also knows that its corresponding patient identification K2 was assigned to the medical device MG.

The mobile device MV from FIG. 2 preferably has as a display unit a display AN and the light-emitting diode LED, the computer R2 being configured to actuate the display AN such that the image data set BX is displayed and that the output of the optical confirmation signal OBS via the LED is brought about.

This is advantageous because even though a display unit AN could, in principle, also be used to output the optical confirmation signal OBS, increased attention of a user could be elicited by using only the LED for outputting the optical confirmation signal OBS. A display AN of a limited size on a mobile device MV, which is preferably a wristband, can thus be used entirely to display the image data set, whereas the confirmation signal OBS can be displayed by the lighting of an LED.

The computer R2 preferably sends a reconfirmation signal RBES via the wireless interface FS to the medical device MG upon receiving the confirmation signal BES. The above-mentioned reconfirmation RBES to the medical device MG is made hereby possible.

The computer R2 preferably determines the image data set BX on the basis of predefined determination steps.

The computer R2 of the mobile device MV preferably determines the image data set BX indirectly from the patient identification KX by the computer R2 reading the image data set BX from the memory unit MEM2. The image data set BX is assigned in the memory unit MEM2 to the data set that represents the patient identification KX.

Figure 3:
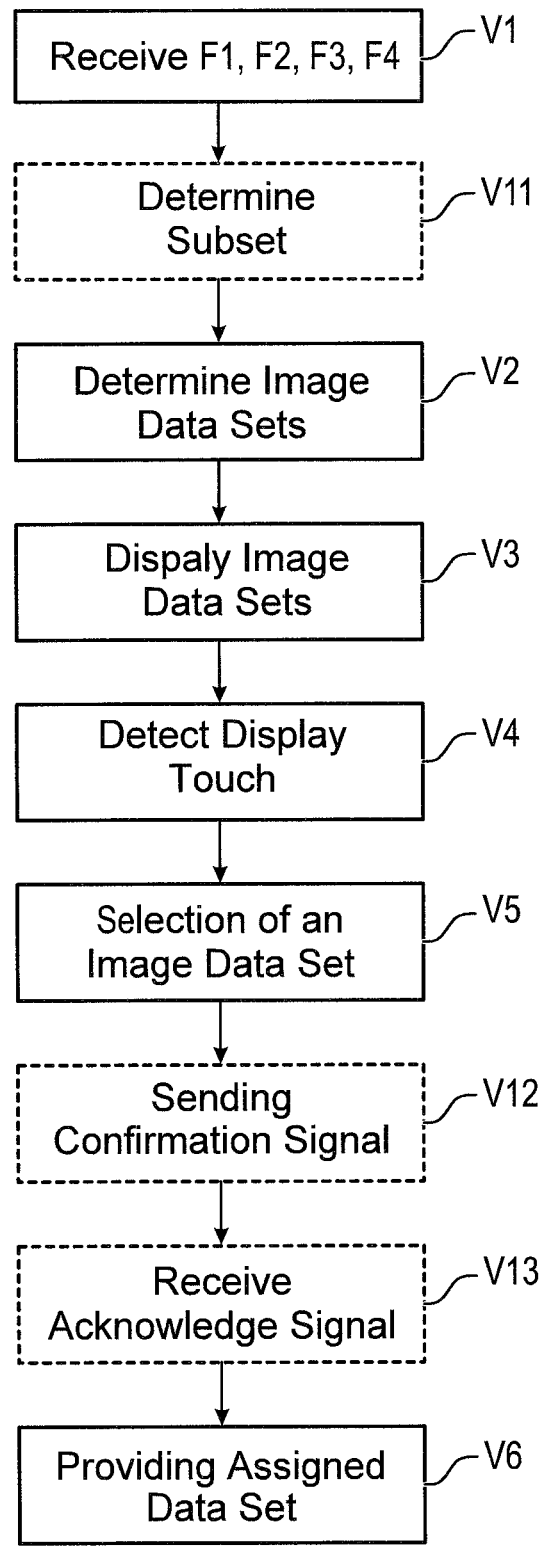
FIG. 3 is a flow diagram showing steps of a method, which steps are carried out by the medical device.

FIG. 3 shows once again a review of the corresponding steps, which are carried out on the medical device MG.

The wireless signals F1, . . . , F4 are received in a first step V1.

The subset of the identifications K1, K2, K3 is determined in a step V11.

The corresponding image data sets B1, B2, B3 are determined in a step V2.

The image data sets B1, B2, B3 are displayed on the display unit A in a step V3.

Touching of a display field A2 is detected in a step V4.

Selection of the image data set B2 is derived in a step V5.

The confirmation signal BES is sent in a step V12, which is preferably to be performed.

The reconfirmation signal RBES is received in a preferable step V13.

The assigned data set K2 is provided in a step V6.

Figure 4:
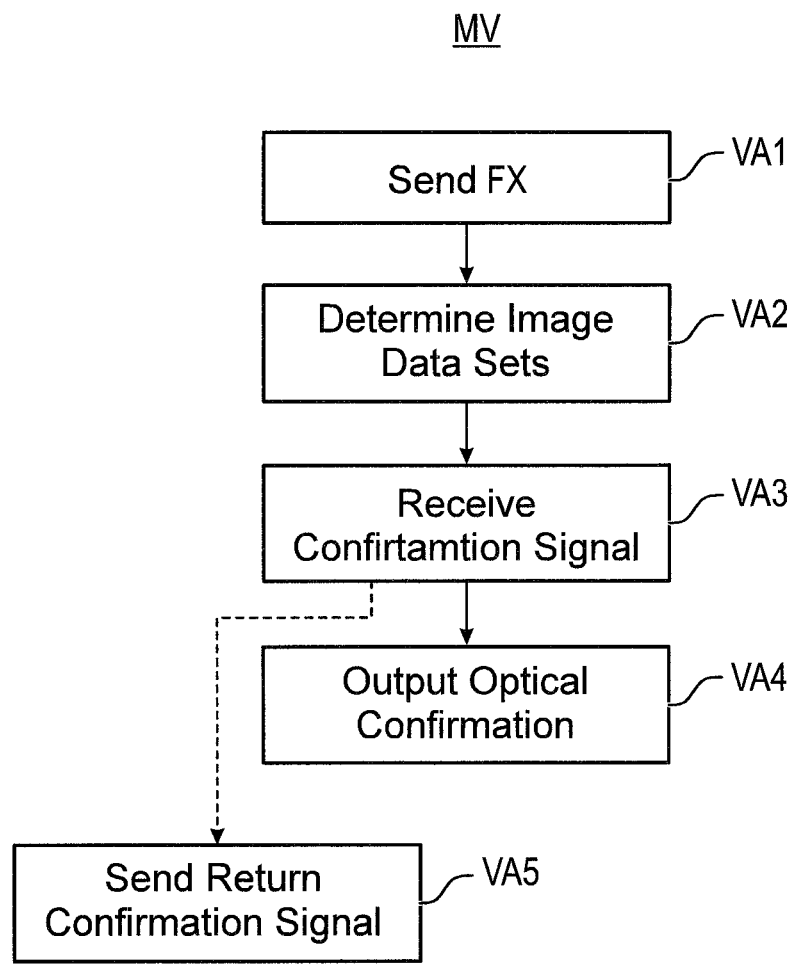
FIG. 4 is a flow diagram showing steps of a method, which steps are carried out by the mobile device.

FIG. 4 shows once again a review of the individual steps, which are carried out on the mobile device MV.

The wireless signal FX, which indicates the patient data set KX, is sent in a step VA1.

An image data set BX is determined directly or indirectly in a step VA2.

The confirmation signal BES is received in a step VA3.

The optical confirmation signal OBS, OBS2 is outputted in a step VA4.

The confirmation signal RBES is sent in an optional step VA5.

The functions of the different computers R, R2 may be implemented by corresponding hardware in the form of a processor. The hardware is preferably hardware that executes software in the form of program code. A process may be embodied in the form of an individual processor or of a system of a plurality of processors. The term "processor" shall not be defined here exclusively as pure hardware for executing software, but it may be embodied as a digital signal processor (DSP), an Application Specific Integrated Circuit (ASIC), a Field Programmable Gate Array (FPGA) or as another type of hardware implementation. The mentioned configuration of the processor may be performed by installing software on the processor when manufacturing the processor or by delivering a communication unit with processor and enclosing a medium containing a computer program product, which can then be installed on the processor.

While specific embodiments of the invention have been shown and described in detail to illustrate the application of the principles of the invention, it will be understood that the invention may be embodied otherwise without departing from such principles.

APPENDIX

List of Reference Designations

| | |
|---|---|
| A, AN | Display unit |
| A1, A2, A3 | Display field |
| ASD | Signal |
| ASI | Display signal |
| ASI | Actuating signal |
| B1, B2, B3, BX | Image data set |
| BES | Confirmation signal |
| DAB | Data bus |

-continued

| | |
|---|---|
| DS | Data network interface |
| F1, . . . , F4, FX | Wireless signals |
| FIG | Finger |
| FS, FS2 | Wireless interface |
| K1, . . . , K4, KX | Patient identification |
| MD | Medical data |
| MEM, MEM2 | Memory unit |
| MG | Medical device |
| OBS, OBS2 | Optical confirmation signal |
| P | Patient |
| R, R2 | Computer |
| RBES | Reconfirmation signal |
| SEN | Sensor |
| SER | Server |
| SES | Sensor interface |
| SIG | Sensor signal |
| SIS | Sensor signal |
| V1, . . . , V4, MV | Mobile device |
| V1, . . . , V6, V11, . . . , V13, VA1, . . . , VA5 | Process step |

What is claimed is:

1. A medical device comprising:
at least one sensor interface configured to detect a sensor signal from a sensor, the sensor signal indicating at least one physiological parameter of a patient;
a data network interface;
a wireless interface configured to receive at least one wireless signal from at least one wristband from among a plurality of wristbands which each generate a respective wireless signal, the at least one wireless signal indicating a patient identification of a mobile device that is carriable on a patient body or physically associated with the patient body;
a touch-sensitive display unit; and
a computer configured to provide medical data, derived from the sensor signal, via the data network interface and configured:
to select a preferred subset of patient identifications based on at least the at least one wireless signal and to directly or indirectly determine respective image data sets based on the patient identifications of the selected subset;
to actuate the display unit such that the respective determined image data sets are displayed in respective display fields, the display unit receiving input from a corresponding display field, the display unit providing a signal as output;
to receive the signal from the display unit and to derive a selection of a certain image data set associated with an assigned patient identification based on the signal;
to make a selection of the certain image data set based on a signal provided by the display unit;
to provide the patient identification assigned to the selected image data set and the medical data associated with the patient identification assigned to the select image data set via the data network interface as output to a data network such that the patient identification assigned to the selected image data set and the medical data associated with the patient identification assigned to the select image data set are configured to be accessed at another time; and
to send a confirmation signal via the wireless interface to a respective mobile device from which a corresponding image data set was derived as the selected image data set.

2. A medical device in accordance with claim 1, wherein the computer is further configured:
to determine a preferred sequence of the image data sets to be displayed based on at least the at least one wireless signal; and
to actuate the display unit such that the respective image data sets are displayed as a function of the determined sequence.

3. A medical device in accordance with claim 1, further comprising a memory unit, wherein the computer is further configured to store the patient identification assigned to the selected image data set in the memory unit.

4. A medical device in accordance with claim 1, further comprising a memory unit, wherein the computer is further configured to determine the respective image data sets directly based on the respective selected patient identifications by the computer determining the respective image data sets from the respective patient identifications based on determination steps provided and predefined by the memory unit.

5. A medical device in accordance with claim 1, wherein the computer is further configured to determine the respective image data sets indirectly based on the respective selected patient identifications by the computer transmitting the respective selected patient identifications to a server and receiving the respective image data sets from the server via the data network interface.

6. A medical device in accordance with claim 1, wherein the computer is further configured
to receive a reconfirmation signal from the respective device from which a corresponding image data set was derived via the wireless interface; and
to perform the providing of the patient identification assigned to the selected image data set via the data network interface only after receiving the reconfirmation signal.

7. A medical device in accordance with claim 1, wherein the confirmation signal prevents the respective mobile device from being assigned to any other medical device.

8. A medical device in accordance with claim 2, wherein the preferred sequence of the image data sets to be displayed is based on signal intensity of at least the at least one wireless signal.

9. A medical device comprising:
at least one sensor interface configured to detect a sensor signal from a sensor, the sensor signal indicating at least one physiological parameter of a patient;
a data network interface;
a wireless interface configured to receive at least one wireless signal from at least one wristband from among a plurality of wristbands which each generate a respective wireless signal, the at least one wireless signal indicating a patient identification of a mobile device that is carriable on a patient body or physically associated with the patient body;
a touch-sensitive display unit; and
a computer configured to provide derived medical data, derived from the sensor signal, via the data network interface and configured:
to select a preferred subset of patient identifications based on at least the at least one wireless signal and to directly or indirectly determine respective image data sets based on the patient identifications of the selected subset;
to actuate the display unit such that the respective determined image data sets are displayed in respective display fields, the display unit receiving input from a corresponding display field, the display unit providing a signal as output based on input from the corresponding display field;

to receive the signal from the display unit and to derive a selection of a certain image data set associated with an assigned patient identification based on the signal;

to make a selection of the certain image data set based on the signal provided by the display unit;

to assign the patient identification to the selected image data;

to assign the patient identification, which is assigned to the selected image data, to the derived medical data;

to provide the patient identification assigned to the selected image data and the derived medical data associated with the patient identification assigned to the selected image data via the data network interface as output to a data network such that the patient identification assigned to the selected image data set and the medical data associated with the patient identification assigned to the select image data set are configured to be accessed at another time; and to send a confirmation signal via the wireless interface to a respective mobile device from which a corresponding image data set was derived as the selected image data set.

10. A medical device in accordance with claim 9, wherein the computer is further configured:

to determine a preferred sequence of the image data sets to be displayed based on the wireless signals; and to actuate the display unit such that the respective image data sets are displayed as a function of the determined sequence.

11. A medical device in accordance with claim 9, further comprising a memory unit, wherein the computer is further configured to store the patient identification assigned to the selected image data set in the memory unit.

12. A medical device in accordance with claim 9, further comprising a memory unit, wherein the computer is further configured to determine the respective image data sets directly based on the respective selected patient identifications by the computer determining the respective image data sets from the respective patient identifications based on determination steps provided and predefined by the memory unit.

13. A medical device in accordance with claim 9, wherein the computer is further configured to determine the respective image data sets indirectly based on the respective selected patient identifications by the computer transmitting the respective selected patient identifications to a server and receiving the respective image data sets from the server via the data network interface.

14. A medical device in accordance with claim 9, wherein the computer is further configured to receive a reconfirmation signal from the respective mobile device from which a corresponding image data set was derived via the wireless interface; and to perform the providing of the patient identification assigned to the selected image data set via the data network interface only after receiving the reconfirmation signal.

15. A medical device in accordance with claim 9, wherein the confirmation signal prevents the respective mobile device from being assigned to any other medical device.

16. A medical device in accordance with claim 10, wherein the preferred sequence of the image data sets to be displayed is based on signal intensity of at least the at least one wireless signal.

* * * * *